(12) United States Patent
Boppart et al.

(10) Patent No.: US 10,524,663 B2
(45) Date of Patent: Jan. 7, 2020

(54) PHASE MEASUREMENT, ANALYSIS, AND CORRECTION METHODS FOR COHERENT IMAGING SYSTEMS

(71) Applicant: The Board of Trustees of the University of Illinois, Urbana, IL (US)

(72) Inventors: Stephen A. Boppart, Champaign, IL (US); Paul Scott Carney, Champaign, IL (US); Nathan Shemonski, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 779 days.

(21) Appl. No.: 15/185,410

(22) Filed: Jun. 17, 2016

(65) Prior Publication Data

US 2016/0367146 A1 Dec. 22, 2016

Related U.S. Application Data

(60) Provisional application No. 62/182,116, filed on Jun. 19, 2015.

(51) Int. Cl.
*A61B 5/00* (2006.01)
*G01B 9/02* (2006.01)

(52) U.S. Cl.
CPC .......... *A61B 5/0066* (2013.01); *A61B 5/7207* (2013.01); *G01B 9/02077* (2013.01); *G01B 9/02091* (2013.01); *A61B 2576/00* (2013.01)

(58) Field of Classification Search
None
See application file for complete search history.

(56) References Cited

U.S. PATENT DOCUMENTS

| 8,532,357 B2 * | 9/2013 | Wollenweber | ........ A61B 5/1114 |
| | | | 382/107 |
| 2005/0054910 A1 * | 3/2005 | Tremblay | ............... A61B 5/055 |
| | | | 600/411 |

(Continued)

OTHER PUBLICATIONS

Ablitt et al., "Predictive Cardiac Motion Modeling and Correction With Partial Least Squares Regression," *IEEE Trans. Med. Imaging*, vol. 23, Issue No. 10, pp. 1315-1324, Oct. 2004.

(Continued)

*Primary Examiner* — Paul A D'Agostino
(74) *Attorney, Agent, or Firm* — Sunstein Kann Murphy & Timbers LLP (57) ABSTRACT

Methods and apparatus for assessing and correcting phase variations and motion artifacts in a coherent tomogram of a sample. Coherent techniques are used scan a broadband optical beam across a sample in a specified scan pattern and to acquire a cube of complex data constituting a full tomogram. Generalized motion of the sample is then quantified based at least on a phase variation measured during the course of scanning the broadband optical beam in the specified scan pattern. Generalized motion includes both actual motion and apparent motion due to organized variation of some physical parameter such as temperature. Intensity structure of speckle imaged during the course of coherently acquiring the full tomograpm may be used to correct for motion of the sample in a plane transverse to a depth axis along the incident beam.

16 Claims, 5 Drawing Sheets
(2 of 5 Drawing Sheet(s) Filed in Color)

(56) References Cited

U.S. PATENT DOCUMENTS

| | | | | |
|---|---|---|---|---|
| 2005/0105097 | A1* | 5/2005 | Fang-Yen | G01B 9/02072 356/497 |
| 2009/0141193 | A1* | 6/2009 | Nakayama | H04N 9/3129 348/751 |
| 2009/0207419 | A1* | 8/2009 | Hwang | G02B 27/48 356/521 |
| 2010/0164495 | A1* | 7/2010 | Takizawa | G01R 33/482 324/309 |
| 2010/0177164 | A1* | 7/2010 | Zalevsky | G01B 11/162 348/46 |
| 2011/0152669 | A1* | 6/2011 | Kassai | A61B 5/055 600/413 |
| 2011/0299064 | A1* | 12/2011 | Sugimoto | G01B 11/162 356/35.5 |
| 2012/0082350 | A1* | 4/2012 | Wollenweber | A61B 6/463 382/128 |
| 2012/0252127 | A1* | 10/2012 | Gregor | G01N 21/51 436/69 |
| 2012/0300277 | A1* | 11/2012 | Cobb | G02B 27/48 359/223.1 |
| 2013/0274590 | A1* | 10/2013 | Auboiroux | A61N 7/02 600/411 |

OTHER PUBLICATIONS

Adie et al., "Computational adaptive optics for broadband optical interferometric tomography of biological tissue," *PNAS*, vol. 109, Issue No. 19, pp. 7175-7180, May 2012.

Ahmad et al., "Real-time in vivo computed optical interferometric tomography," *Nat. Photonics*, vol. 7, Issue No. 6, pp. 444-448, Jun. 2013.

Felberer et al., "Adaptive optics SLO/OCT for 3D imaging of human photoreceptors in vivo," *Biomedical Optics Express*, vol. 5, Issue No. 2, pp. 439-456, Feb. 2014.

Kumar et al., "Subaperture correlation based digital adaptive optics for full field optical coherence tomography," *Optics Express*, vol. 21, Issue No. 9, pp. 10850-10866, May 2013.

Lee et al., "Motion correction for phase-resolved dynamic optical coherence tomography imaging of rodent cerebral cortex," *Optics Express*, vol. 19, Issue No. 22, pp. 21258-21270, Oct. 2011.

Liu et al., "Phase registration based on matching of phase distribution characteristics and its application in FDOCT," *Optics Express*, vol. 21, Issue No. 11, pp. 13241-13255, Jun. 2013.

Mariampillai et al., "Speckle variance detection of microvasculature using swept-source optical coherence tomography," *Optics Letters*, vol. 33, Issue No. 13, pp. 1530-1532, Jul. 2008.

Ralston et al., "Real-time interferometric synthetic aperture microscopy," *Optics Express*, vol. 16, Issue No. 4, pp. 2555-2569, Feb. 2008.

Vakoc et al., "Statistical Properties of Phase-Decorrelation in Phase-Resolved Doppler Optical Coherence Tomography," *IEEE Trans. Med. Imaging*, vol. 28, Issue No. 6, pp. 814-821, Jun. 2009.

White et al., "In vivo dynamic human retinal blood flow imaging using ultra-high-speed spectral domain optical Doppler tomography," *Optics Express*, vol. 11, Issue No. 25, pp. 3490-3497, Dec. 2003.

Xu et al., "Phase-shift extraction for phase-shifting interferometry by histogram of phase difference," *Optics Express*, vol. 18, Issue No. 23, pp. 24368-24378, Nov. 2010.

* cited by examiner

PHASE MEASUREMENT, ANALYSIS, AND CORRECTION METHODS FOR COHERENT IMAGING SYSTEMS

The present application claims the priority of U.S. Provisional Patent Application 62/182,116, filed Jun. 19, 2015, and incorporated herein by reference.

This invention was made with government support under EB013723 awarded by the National Institutes of Health and CBET1445111 awarded by the National Science Foundation. The Government has certain rights in the invention.

TECHNICAL FIELD

The present invention relates to methods for measuring phase variations during the course of acquiring a three-dimensional image, and, more particularly, to correcting phase due to motion in axial and/or transverse directions.

BACKGROUND ART

Motion in tissues has always been problematic for in vivo imaging in high-resolution optical systems. The difficulties imposed by involuntary retinal and cardiac movements with respect to acquisition and processing of artifact-free in vivo data are discussed, respectively, by Považay et al., "*Impact of enhanced resolution, speed and penetration on three-dimensional retinal optical coherence tomography,*" Opt. Exp., vol. 17, pp. 4134-50 (2009), and Ablitt et al., "*Predictive cardiac motion modeling and correction with partial least-squares regression,*" IEEE Trans. Med. Imaging, vol. 23, pp. 1315-24 (2004), both of which papers are incorporated herein by reference.

A number of approaches have been used both to correct, and to avoid, motion. For cardiac and respiratory imaging, synchronization with the beating heart or imaging between breaths, respectively, is common in magnetic resonance imaging and ultrasound. When motion is involuntary and random in nature, though, the only options are to scan fast enough to avoid motion, compensate for motion during imaging, or correct the motion in post-processing. In optical coherence tomography (OCT), 2-D cross sections are easily acquired without motion artifacts, but full 3-D volumes often still require some amount of motion compensation or correction—especially for in vivo retinal imaging.

For motion correction in post-processing, motion must be measured in some way. Depending on the application, the required precision of the measured motion will change. For traditional amplitude imaging, the required precision depends only on the resolution of the imaging system. Thus, for OCT, assuming features with sufficient contrast exist, separate incoherent imaging systems are often used in conjunction with the acquired data to rapidly track and correct for motion, as exemplified, for example, by Felberger et al., "*Adaptive Optics SLO/OCT for 3D imaging of human photoreceptors in vivo,*" Biomed. Opt. Exp., vol. 5, pp. 439-56 (2014), incorporated herein by reference. For imaging modalities such as Doppler OCT, the required precision of axial motion tracking is well below the resolution of the system as these modalities rely on the phase of backscattered light. It is possible, though, to utilize spatial oversampling and the measured phase in depth to correct this motion, as taught by White et al., "*In vivo dynamic human retinal blood flow imaging using high-speed spectral domain optical coherence tomography,*" Opt. Exp., vol. 11, pp. 3490-97 (2003), incorporated herein by reference. Transverse motion correction in Doppler OCT requires the same precision as traditional OCT amplitude imaging, and thus can use similar tracking and correction techniques as other OCT imaging systems.

Interferometric Synthetic Aperture Microscopy (ISAM), Computational Adaptive Optics (CAO), Digital Adaptive Optics (DAO), and Holoscopy are all computed imaging techniques which can computationally correct defocus and optical aberrations, but are known to have especially high sensitivity to motion. This is true for even the swept-source full-field techniques (DAO and Holoscopy). Even though the transverse phase relationship is preserved for each individual wavelength of light, the full spectrum, which is required for the reconstruction, is measured over time, and is therefore susceptible to motion. In addition, these techniques may actually be more susceptible to motion due to the long interrogation length of each point in the sample.

Axially, the stability requirements of computed optical interferometric techniques in general can be the strictest, as they utilize the phase of the measured data. This means that even motion on the order of the wavelength of light can interfere with the desired reconstruction.

For the transverse dimensions, defocus and aberration correction techniques are unique in that the tolerable level of motion can be well below the resolution of the imaging system. This occurs in the presence of aberrations where, when diffraction-limited performance is not achieved at the time of imaging, the stability requirements for correcting the aberrations actually increases due to a longer interrogation length. Therefore, a separate incoherent imaging system with the same non-diffraction-limited performance cannot be used to measure motion with the required precision because of the lack of sharp high-contrast features.

Prior art methods required either stable data at the time of imaging or use of a phase reference, such as a coverslip placed on the sample or tissue, to compensate for optical path length fluctuations, as taught by Ralston et al., "*Real-time interferometric synthetic aperture microscopy,*" Opt. Exp., vol. 16, pp. 2555-69 (2008), which is incorporated herein by reference. Additionally, it has been shown that motion could be corrected by using only the acquired OCT data for numerical defocus correction and other phase-resolved techniques, however these techniques, described in the following references, both incorporated herein by reference, are all, necessarily, restricted to one- or two-dimensional motion correction:

Lee, et al., "*Motion correction for phase-resolved dynamic optical coherence tomography imaging of rodent cerebral cortex,*" Opt. Express, vol. 19, pp. 21258-70 (2011); and Liu, et al., "*Phase registration based on matching of phase distribution characteristics and its application in FDOCT,*" Opt. Exp., vol. 21, pp. 13241-55 (2013).

Phase stability assessment has also been applied in a tomographic context, by White et al., "*In vivo dynamic human retinal blood flow imaging using ultra-high-speed spectral domain optical Doppler tomography,*" Opt. Exp., vol. 11, pp. 3490-97 (2003), which is incorporated herein by reference. White (2003) required incidence of light onto the sample by reflection from a fixed mirror so that all phase differences could be attributed solely to movement within the sample.

For many applications, however, it is desirable that a method be provided for assessing stability using the phase while allowing for a scanned imaging configuration. This however adds the complication of assessing stability in all three dimensions, as is provided in accordance with the teachings of the present invention, as now described.

SUMMARY OF EMBODIMENTS OF THE INVENTION

In accordance with embodiments of the invention, methods and apparatus are provided for measuring phase variations in a coherent three-dimensional image of a sample. A method, in accordance with one embodiment, has steps of:
  generating a broadband optical beam incident on the sample along a depth axis;
  scanning the broadband optical beam across the sample in a specified scan pattern;
  interfering light scattered by the sample with a reference beam derived from the broadband optical beam;
  measuring the intensity of the interfered light on at least one photosensitive element;
  processing the collected data to generate a cube of complex data including both amplitude and phase data constituting a full tomogram; and
  after acquisition of the full tomogram, quantifying generalized motion to the sample based at least on a measured phase variation measured during the course of scanning the broadband optical beam in the specified scan pattern, wherein the phase variation is measured based solely on a frame of reference tied to the sample.

In accordance with alternate embodiments of the present invention, a further step may be provided of correcting the cube of complex data for the generalized motion, thereby creating a phase-stable cube of complex data. Additionally, steps of either computationally refocusing or computationally correcting aberrations in the cube of complex data may be provided.

In accordance with other embodiments of the invention, the measured phase variation may be along an axial direction, and scanning the broadband optical beam in the specified scan pattern may include scanning the broadband optical beam across the sample in a transverse plane along a fast axis and a slow axis. There may also be a further step of correcting at least one of actual and apparent motion in the full tomogram based on the measured phase variation, and, more particularly, correcting for generalized movement along the fast axis by interpolation of a corresponding frame of the full tomogram.

In other embodiments, measured phase variations may be derived by:
  calculating a plurality of phase differences between A-scans acquired at different points in time;
  averaging the complex data along the depth axis and extract the resulting phase to create a 2D phase-variation map;
  integrating a plurality of phase differences along the slow axis to derive a total phase change; and
  for each fixed depth, subtracting the phase motion map from the phase of the complex tomogram.

In accordance with another aspect of the invention, a method is provided for acquiring a motion-corrected coherent three-dimensional image of a sample. The method has steps of:
  generating a broadband optical beam incident on the sample along a depth axis;
  scanning the broadband optical beam across the object in a specified scan pattern substantially transverse to the depth axis;
  interfering light scattered by the sample with a reference beam derived from the broadband optical beam;
  measuring the intensity of the interfered light on at least one photosensitive element;
  processing the collected data to generate a cube of complex data including both amplitude and phase data constituting a full tomogram;
  concurrently imaging backscattered light from the same sample resulting in a sequence of at least two speckle images; and
  after acquisition of the full tomogram, correcting for motion of the sample in the transverse plane based on the intensity structure of the speckle.

In accordance with other embodiments, scanning the broadband optical beam in the specified scan pattern may include scanning the broadband optical beam across the sample in a transverse plane along a fast axis and a slow axis, as well as concurrently imaging speckle of the object includes illuminating the surface of the object with spectrally-coherent light or spatially-coherent light.

In further embodiments of the invention, generating a broadband optical beam incident on the sample may include directing light onto the sample from a source chosen from a group of low-coherence sources including a superluminescent diode, a light-emitting diode, and a broadband laser. Generating a broadband optical beam incident on the sample may include steering the broadband optical beam with a galvanometric steering mirror, or, otherwise.

In accordance with yet further embodiments of the present invention, the method has a further step of correcting at least one of actual and apparent motion in the full tomogram based on the measured phase variation, or by interpolation of a corresponding frame of the full tomogram.

In further embodiments still, addition steps are provided of
  deriving speckle tracking data from phase statistics of imaged speckle at the plurality of axial steps along the depth axis; and
  correcting the full tomogram for any transverse motion on the basis of the speckle tracking data prior to correction for any motion along the depth axis.

The sample may include tissue of a living animal with a closed circulatory system, and scanning the broadband optical beam across the object in a specified scan pattern substantially transverse to the depth axis includes selecting a scanning region substantially devoid of vasculature. The coherent light may be characterized by a wavelength within a spectral range between 520 nm and 590 nm.

In accordance with another aspect of the present invention, an apparatus is provided for jointly acquiring phase variations and transverse motion in a tomogram of a sample. The apparatus has a source for generating a broadband optical beam, steering optics for scanning the broadband optical beam across the sample in a plane substantially transverse to a depth axis, an interferometer for interfering light scattered by the sample with a reference beam derived from the broadband optical beam, and a first detector for generating a frame of complex data including both amplitude and phase data. The apparatus also has a source of coherent light for illuminating the sample and generating speckle at a surface of the sample, a second detector for generating an image of the speckle from the backscattered light from the sample, and a processor adapted to derive, after acquisition of a full tomogram, phase variations and to correct for motion of the sample in the transverse plane based at least on the intensity of the speckle. More particularly, the source for generating a broadband optical beam may be a superluminescent diode, although other sources may be used as well, within the scope of the present invention.

In accordance with yet another aspect of the present invention, a computer product for use on a computer system is provided for measuring phase variations in a coherent three-dimensional image of a sample. The computer program product has a computer-usable tangible medium having computer-readable program code fixed thereon, the computer-readable program code including:

program code for inputting a plurality of frames of complex data based on interference of light scattered by the sample with a reference beam at a plurality of axial steps along a depth axis;

program code for inputting speckle imaging data derived from a surface of the sample at the plurality of axial steps; and program code for quantifying phase variations along the depth axis based jointly at least on measured phase fluctuations in an aggregate of the plurality of axial steps and phase statistics of the speckle.

The computer product may also have program code for calculating a plurality of phase differences between axial steps along the depth axis, program code for averaging the complex data along the depth axis and extracting the phase to create a 2D phase map, program code for integrating the plurality of phase differences along a slow axis to derive a total phase change, program code for optionally filtering the phase map, and program code where for each fixed depth, the phase motion map is subtracted from the phase of the complex tomogram.

In accordance with other embodiments of the invention, the computer product may additionally have program code for correcting for movement along a fast axis by interpolation of a corresponding frame of the full tomogram, and/or program code for deriving speckle tracking data from intensity of the imaged speckle, as well as program code for correcting the full tomogram for any transverse motion on the basis of the speckle tracking data prior to correction for any motion along the depth axis.

BRIEF DESCRIPTION OF THE DRAWINGS

The present patent or application file contains at least one drawing executed in color. Copies of this patent with color drawing(s) will be provided by the Patent and Trademark Office upon request and payment of necessary fee.

The foregoing features of the invention will be more readily understood by reference to the following detailed description, taken with reference to the accompanying drawings, in which:

FIGS. 4A, 4B and 4C are, respectively, versions of FIGS. 4D, 4E and 4F that have been computationally refocused, in accordance with embodiments of the present invention.

FIG. 5B is the same plane after using speckle tracking, in accordance with an embodiment of the present invention. The plane shown in FIG. 5C has been computationally refocused in accordance with an embodiment of the present invention after 2-D motion correction, while

DETAILED DESCRIPTION OF EMBODIMENTS OF THE INVENTION

Various phase measurement and motion correction techniques are encompassed within the scope of the present invention. In accordance with one class of techniques, phase variations alone of the acquired OCT data are relied upon to correct for small axial motion. This method is very general, is found to have few prior assumptions which need to be met, and does not require the use of a coverslip on the sample or tissue. In accordance with another class of techniques, additional hardware is employed to track transverse motion. By illuminating the sample with a narrowband laser diode, and imaging the resulting speckle patterns onto a camera, motion can be tracked at high speeds and with high precision, even in the presence of aberrations. Combinations of the foregoing techniques are sensitive enough to correct 3-D motion for in vivo numerical defocus and aberration correction.

Definitions

The term "image" shall refer to any multidimensional representation, whether in tangible or otherwise perceptible form, or otherwise, whereby a value of some characteristic (amplitude, phase, etc.) is associated with each of a plurality of locations corresponding to dimensional coordinates of an object in physical space, though not necessarily mapped one-to-one thereonto. Thus, for example, the graphic display of the spatial distribution of some field, either scalar or vectorial, such as brightness or color, constitutes an image. So, also, does an array of numbers, such as a 3D holographic dataset, in a computer memory or holographic medium. Similarly, "imaging" refers to the rendering of a stated physical characteristic in terms of one or more images.

A "coherent image" is an image obtained using coherence properties of light, thus comprising both amplitude and phase information.

The terms "object," "sample," and "specimen" shall refer, interchangeably, to a tangible, non-transitory physical object capable of being rendered as an image.

The term "low-coherence" (or "broadband," as used interchangeably herein) applies to a source of illumination for which the coherence length is shorter than 30 μm, and/or for which $\Delta k/k_0$ is at least 10%, with $k_0$ denoting the central wavenumber of the spectrum illuminating the sample, while $\Delta k$ denotes the range of illuminating wavenumbers. It is to be understood that, within the scope of the present invention, the wavelength of the source need not be fixed in time, indeed, the wavelength of the source may be swept in time.

"Spectrally coherent light," as the term is used herein, refers to light that, while multichromatic, maintains a relative phase-relationship across frequencies that is fixed to some degree.

A "fluctuation" shall denote a random variation in time of a parameter from a time-averaged value.

"Variation," as the term is used herein, and unless the context specifically requires otherwise, shall denote a change with time.

A parameter shall be referred to as "complex" when it has real and imaginary parts, and may be represented as an $ae^{i\Phi}$, where a is the amplitude, and $\phi$ is the phase of the parameter. The parameter in question may be an optical field at a specified frequency, for example, or it may be the susceptibility $\chi$ of a sample.

"Stability" is a measure of the constancy of a parameter, or of its amplitude or phase taken separately, with respect to time. The measure of constancy, specifically, is that all statistical properties of the parameter as a function of time are time-independent.

"Axial" refers to a direction, the "depth axis," within a sample that is along, or parallel to, a beam the propagation direction of light used to probe the sample.

"Transverse" refers to a plane that is perpendicular to an axial direction.

"Generalized motion" shall encompass either organized motion of all, or part, of the sample, or organized variation with time of some physical parameter, such as temperature, that gives rise to an organized phase variation. Generalized motion that is due to organized translation or rotation of all or portion of the sample may be referred to herein, and in any appended claims, as "actual motion." Generalized motion that is due to organized variation of a physical parameter other than position or orientation in space may be referred to as "apparent motion."

A "tomogram" shall refer to a three-dimensional image, with "image" as defined above. A tomogram may be of values of a complex parameter, such as the susceptibility of a sample.

A "full tomogram" is a tomogram of a simply-connected volume, wherein any simple closed curve in the volume may be continuously (to within sampling limits) shrunk to a point.

A "cube of complex data" shall refer to a full tomogram of values of a complex parameter.

A "phase stable cube of complex data" shall refer to a cube of complex data, wherein a phase associated with any voxel, as referenced to a fiducial phase defined solely with respect to values assumed by the complex variable within the sample, shall constitute a stochastic variable, the statistical distribution of which, with respect to time, shall be invariant with respect to time.

A phase variations measured independently of any reference to a coverslip or to any fiducial phase in a frame of reference outside that of the sample shall be referred to as a "phase variation based solely on a frame of reference tied to the sample."

"Correcting" means removing generalized motion from measured data such that the resulting data is as though measured in the absence of generalized motion.

A first embodiment of the present invention is now described with reference to FIG. 1, where a spectral domain optical coherence tomography (SD-OCT) system is designated generally by numeral 100. It is to be understood that the SD-OCT system 100 is depicted by way of example only, and without loss of generality, insofar as the present invention may be advantageously employed in various tomographic imaging systems, and, more particularly, in optical tomographic imaging systems.

Figure 1:
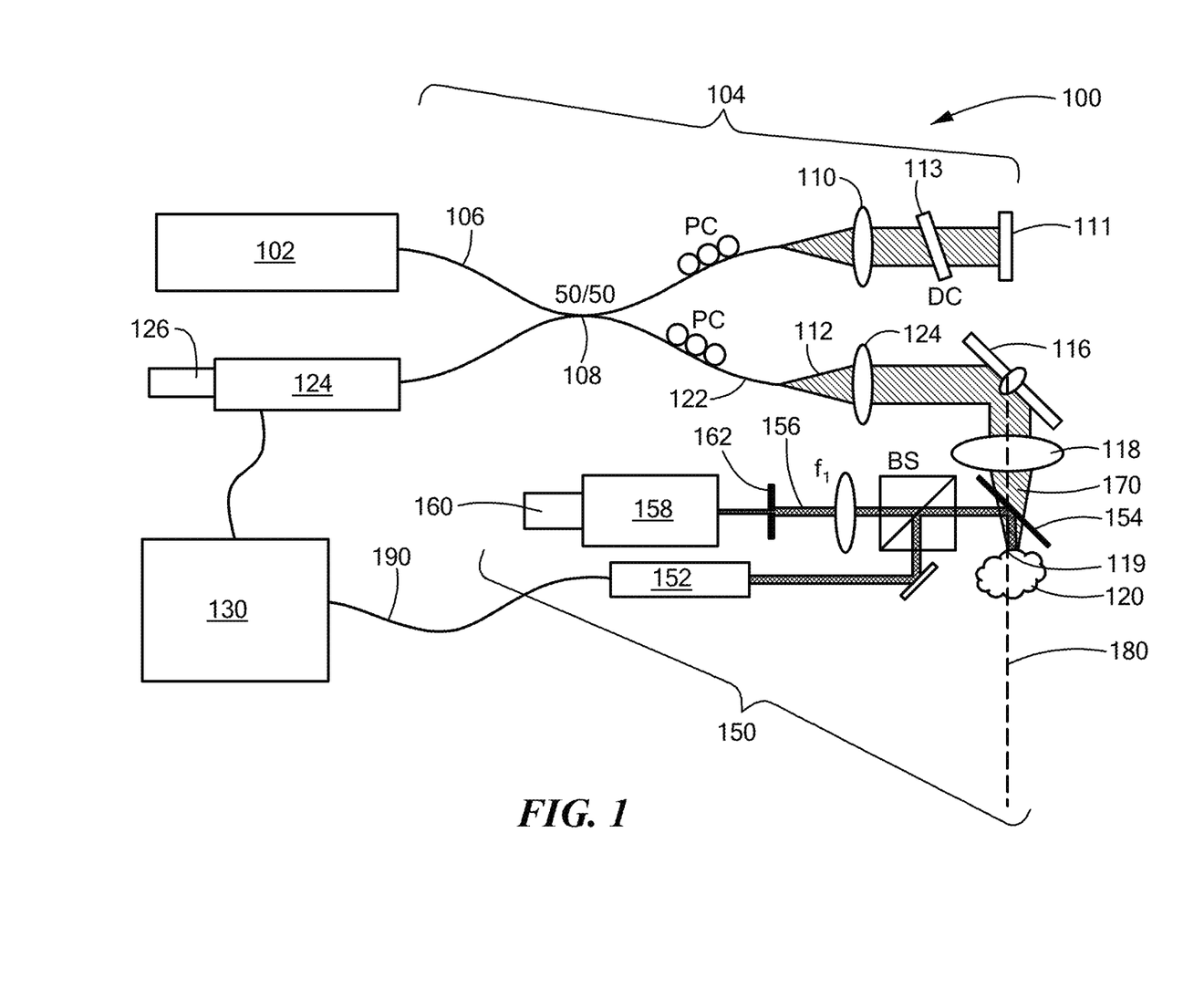
FIG. 1 is a schematic representation of a motion-compensated spectral domain optical coherence tomography system in accordance with an embodiment of the present invention.

Referring to FIG. 1, a source 102 of broadband radiation introduces light into an interferometer designated generally by numeral 104. Source 102 is preferably a superluminescent diode (SLD), and for heuristic convenience may be referred to as such in the remainder of the present description, however the present invention may be practiced using various types of sources of illumination. For example, a light-emitting diode (LED) or broadband laser may be employed, as well, within the scope of the present invention. Use of an SLM with a spectral bandwidth of 170 nm (FWHM), for example, provides a measured axial resolution of 6 μm (FWHM) in air. In the embodiment depicted by way of example, light from source 102 is coupled into optical fiber 106 and split by beamsplitter 108 into a sample path 112 and a reference path 110. Sample beam 112 is collimated by collimating optic 114, and directed by steering mirror 116, via focusing optic 118, onto sample 120, which is typically biological tissue. Steering mirror 116 is preferably galvanometer-driven, although the use any steering mirror lies within the scope of the present invention. Focusing optic 118 is an objective lens, preferably an achromatic doublet with a focal length of 40 mm. Scattered light from sample 120 is coupled into optical fiber arm 122 by lens 124, where it is interfered with light returned from reference path 110 by reflection at mirror 110, dispersed by spectrometer 126, and detected by detector array 128. Detector array 128 is comprised of one or more square-law photosensitive elements, such that detector array 128 measures the intensity of the interfered light at one or more distinct pixel positions. Full-field scanning methods, wherein the entirety of a surface of sample 120 is imaged concurrently, may fall within the scope of the present invention, in certain embodiments, as well. In a preferred embodiment, detector array 128 is a 1024-pixel line scan camera operated at a line rate of 92 kHz. As routinely practiced in OCT systems, dispersion compensation 113 and polarization controllers PC may be provided within either sample or reference path 110 of interferometer 104. Interferometric signal data from detector array 128 is coupled to processor 130 where it is processed in accordance with routine OCT data processing, and, further, as discussed below. OCT data processed to provide images at successive depths into sample 120 are referred to herein as A-scans. The successive depths into sample 120 may be referred to as "axial steps." The axis into sample 120 along the propagation direction of incident beam 170 may be referred to, herein, as $\hat{z}$, the "longitudinal axis," the "depth axis," or the "optical axis" 180.

More particularly, scanning mirror 116 provides a transverse field-of-view, which, in one embodiment, consists of 600×600 pixels$^2$. Combined with a custom waveform (85% linear and 15% fly-back), an effective frame rate was 127.7 frames-per-second (FPS), in one embodiment. Insofar as an OCT tomogram is acquired by raster-scanning a point 119 across the sample 120, a first transverse dimension defines a fast axis while the orthogonal transverse dimension defines a slow axis. Within the scope of the present invention, point 119 may be scanned across sample 120 in any specified scan pattern, subject to system design considerations by an instrument designer of ordinary skill in the art.

Referring, further, to FIG. 1, a speckle-tracking subsystem, designated generally by numeral 150, is also provided. Speckle-tracking subsystem 150 uses a coherent source 152 to illuminate a small region of sample 120 via a dichroic beamsplitter 154 positioned between the sample 120 and the objective lens 118. Other coupling schemes are within the scope of the present invention. In one embodiment of the invention, coherent source 152 is a green laser, such as a Model DJ532-10 available from Thorlabs, Inc. of Newton, N.J., which provides a monochromatic beam at 532 nm. The illuminated region of the sample 120 has an illuminated area characterized by a linear dimension on the order of 2 mm.

Coherent light 156 either reflected or backscattered from sample 120 is imaged onto camera 160, which may be a CCD array with a multi-element focusing arrangement 158. Camera 160 may be referred to, herein, for convenience, either as "CCD 160" or as "speckle camera 160." In a preferred embodiment of the invention, camera 160 is an 8.8 megapixel CCD USB3.0 camera, such as a Model FL3-U3-88S2C-C, available from Point Grey Research of Richmond, Canada. By way of non-limiting example, focusing arrangement 158 may be a combination of a 40-mm focal-length doublet and a multi-element objective. An iris 162 may be placed before focusing arrangement 158 to control the N.A. of the imaging system. A tighter focus is desirable to increase oversampling of the speckle pattern, but must be traded off against light intensity to achieve adequate signal-to-noise.

The wavelength of coherent source 152 is preferably chosen to minimize any contribution of particulate flow within sample 120 on an analysis of speckle variance derived from the surface of sample 120. Thus, insofar as sample 120 constitutes skin or other blood irrigated tissue, it is preferable that the wavelength of coherent source 152 lie within a band of blood cell absorption, so as to minimize contrast degradation of the speckle signal. More particularly, a wavelength within the band of 520-590 nm is preferred. In other embodiments of the invention, the wavelength of coherent source 152 may advantageously lie shortward of 460 nm.

The speckle image on CCD 160 resulting from focusing coherent light 156 reflected from sample 120 is typically a small region (approximately 150×250 pixels$^2$). An even smaller subset of CCD 160 may be used for tracking (100×100 pixels$^2$). The speckle subsystem 150 is synchronized with the SD-OCT system using an external trigger cable 190. The frame rate of camera 160 may, in certain cases, ultimately be limited by camera firmware or otherwise. In an exemplary embodiment, a camera exposure time of 8.6 ms was used, the frame rate was limited to 28 frames per second (FPS), and the OCT system 100 was operated at 127.7 FPS, although those times are provided solely by way of example, and without limitation. In the exemplary case described, 5° C.T frames 202 were acquired for every one speckle image 220.

Figure 2A:
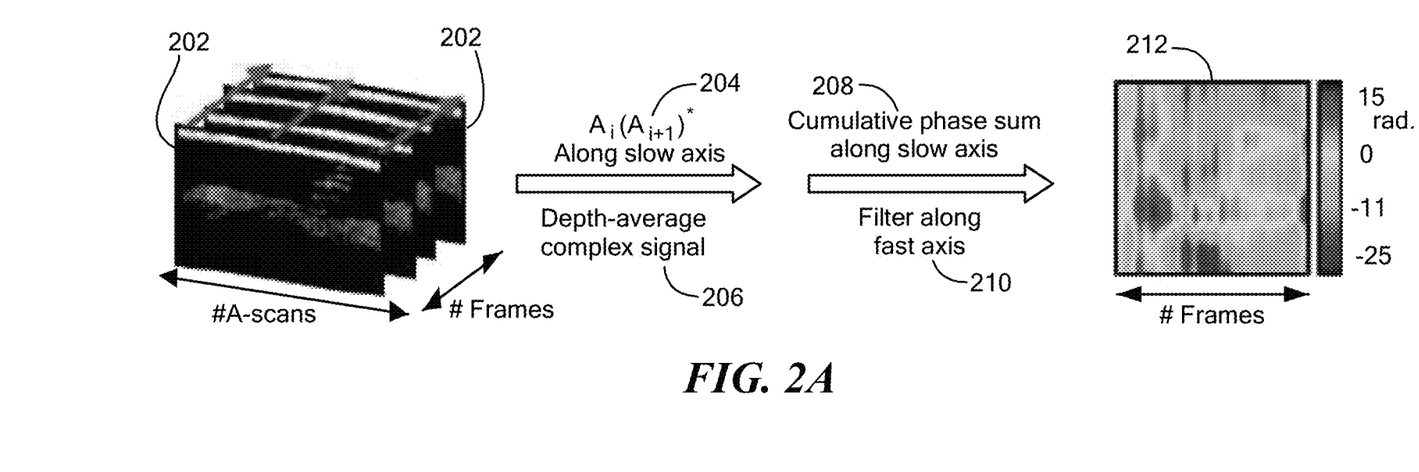
FIG. 2A is a flowchart depicting axial motion tracking without a coverslip, in accordance with an embodiment of the present invention.
Figure 2B:
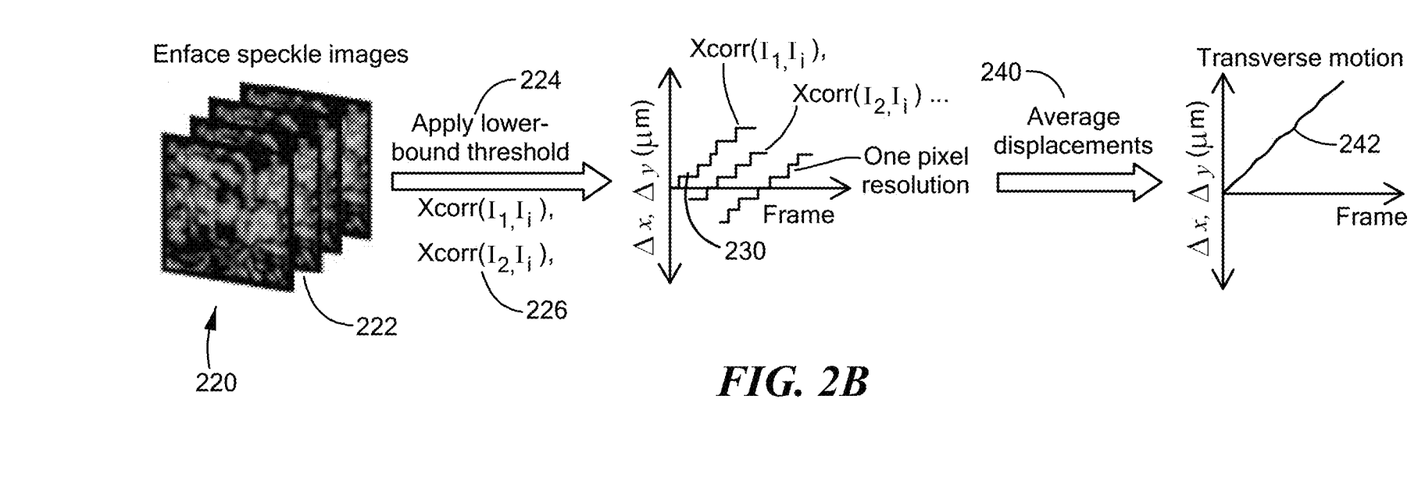
FIG. 2B is a flowchart depicting sub-pixel speckle tracking, in accordance with an embodiment of the present invention.

Whereas prior art phase stability assessment modalities required a stationary ("motion mode," or M-mode) imaging modality, as discussed in the Background section with respect to White (2003), the present invention teaches the scanning, acquisition and analysis of an entire three-dimensional OCT tomogram, as now described in detail with reference to FIGS. 2A and 2B. Parallel frames 202 correspond to data in the depth/fast-axis plane, each frame 202 corresponding to a distinct position along the slow axis. In accordance with preferred embodiments of the invention, complex data are obtained using standard Fourier domain OCT processing steps of resampling, dispersion compensation, and FFT, as described in detail, for example, in Drexler et al., *Optical Coherence Tomography: Technology and Applications* (2$^d$ ed.) (2015) (hereinafter, "Drexler 2015") which is incorporated herein by reference.

Phase differences between successive A-scans along the slow axis are then calculated (in step 204) using complex conjugate multiplication, $A_i(A_{i+1})^*$, insofar as the phase of the product is the difference in phase between scans. The complex data are then averaged over depth (in step 206) resulting in a weighted circular mean, with weighting favoring higher signal-to-noise ratio (SNR) values.

Phase is then extracted from the complex data, with the phase in the first fast axis line set to zero, and summed (in step 208) along the slow axis (or, equivalently, in time) to yield a total phase change, filtered along to the fast axis (in step 210) to smooth the phase map. The filtering is optional, and could be applied in both dimensions, as well. Possible filters include, but are not limited to, mean filter, median filter, bilateral edge-preserving filter, etc., yielding a phase map 212 which depicts axial motion (in radians of phase) as a function of position on the face of sample 120 (shown in FIG. 1). The foregoing depiction of motion in terms of phase constitutes "quantifying variation of phase."

The resultant phase map is finally conjugated and applied to each depth in the OCT data. This OCT data, or cube of complex data is now considered 'phase stable', or a phase stable cube of complex data because the generalized motion has been corrected.

It should be noted that the phase differences between A-scans need not be on successively-acquired A-scans. Phase differences could, for instance, be calculated between two A-scans in two separate frames as long as the A-scans are acquired from nearby locations within approximately one beam width of each other.

Of course, phase differences can also be calculated directly rather than through complex conjugate multiplication by computing the phase of each point and subtracting them. The phase data can then for instance be averaged along depth, or, alternatively, a histogram of phase difference can be analyzed, as taught by Xu, "Phase shift extraction for phase shifting interferometry," *Opt. Exp.*, vol. 18, pp. 24368-78 (2010), which is incorporated herein by reference. These alternative averaging techniques lead to a phase map similar to that described above. It should be recognized by one skilled in the art that other techniques such as maximum a priori estimates can be used to estimate the axial motion at each point in the sample from phase differences.

Assessment and correction of motion in a plane transverse to optical axis 180 (shown in FIG. 1) is performed, in accordance with an embodiment of the present invention, as now described with reference to FIG. 2B. Speckle data from speckle camera 160 are shown in the time-ordered stack 220 of en face speckle image frames 222 (referred to as $I_i$). Time-ordered stack 220 may be referred to herein as a "speckle movie." The speckle data are preferably thresholded from below (in step 224), allowing only bright speckles to be tracked and suppressing some background noise. Each speckle frame 222 is cross-correlated (in step 226) with prior ($I_{i-1}$) and subsequent ($I_{i+1}$) frames until the normalized cross-correlation coefficient drops below a specified value, for which a normalized cross-correlation coefficient cutoff of 0.3 is preferred. Thus, for each frame $I_i$ a cross-correlation was used to determine the 2-D movement with respect to each other frame. $I_j$. These traces 230 as a function of time are labeled as Xcorr($I_i$, $I_j$) in FIG. 2 and only have single-pixel accuracy. Multiple piecewise displacement traces 230 are found, with each trace used a different speckle frame as zero reference, and each providing a resolution of one camera pixel as shown in the bottom center of FIG. 2. These traces 230 are then aligned and averaged (in step 240) to compute the final sub-pixel displacements 242 as a function of time.

Using the sub-pixel displacements, movement along the fast axis is corrected by shifting/interpolating the corresponding OCT frame 202 by the calculated number of pixels using the interp1 function in MATLAB, for example.

Motion correction along the slow axis may be accomplished as now described, by way of example. First, a blank volume of data is created in memory, twice as large as the original tomogram volume (i.e., the aggregate volume of the frames 202). Using the displacements along the slow axis, as derived above, the position of each fast-axis-corrected frame along the slow axis is calculated. Using these positions, the fast-axis frames are inserted into the blank volume by rounding to the nearest half-pixel. Any frames with duplicate positions are discarded. The data is then down-sampled, again using the interp1 function in MATLAB, for example. This allows interpolation of missing data, and returns the tomogram volume back to the original size.

In accordance with embodiments of the present invention, phase corrections for any generalized motion (including all phenomena that vary the phase) along the optical axis may be performed separately from, or in conjunction with, corrections for any transverse motion derived using the speckle tracking data described above. In a preferred embodiment, described by way of example, corrections are first applied for any transverse motion, and then the phase corrections for any motion along the optical axis are performed, as described above. Changes in temperature distribution or pressure distribution, for example, may also give rise to phase variations during the course of acquiring tomographic data which are indistinguishable from axial motion. In this document, it is understood that 'motion' refers to both actual motion of the sample, or apparent/relative motion such as that resulting from refractive index changes or movement of the scanning system.

Once generalized motion has been quantified, as taught in the foregoing description, the generalized motion may be corrected for in the cube of complex data, using techniques such as, but not limited to, the ones described in the foregoing description. Once generalized motion has been separated from the cube of complex data, all remaining time dependency in the cube of complex data is random, which is to say, with respect to the phase in particular, that a phase-stable cube of complex data has been created. In accordance with further embodiments of the present invention, refocusing is performed by adjusting the $z_4$ (defocus) Zernike polynomial as described in Adie et al., "*Computational adaptive optics for broadband optical interferometric tomography of biological tissue,*" Proc. Nat. Acad. Sci. U.S.A., vol. 109, pp. 7175-80 (2012), which is incorporated herein by reference. Kumar et al., "*Numerical focusing methods for full field OCT: a comparison based on a common signal model,*" Opt. Exp., vol. 22, pp. 16061-78 (2014) also addresses focus correction, and is incorporated herein by reference. To perform refocusing throughout all depths, two axially separated planes positioned at $z=z^1$ and $z=z^2$ are first manually refocused. Using the two $z_4$ values ($z_4^1$ and $z_4^2$) as references, $z_4$ is varied linearly along depth to refocus the entire volume. Astigmatism introduced from the dichroic mirror 154 (shown in FIG. 1) may be corrected using the $z_6$ Zernike coefficient, which is kept constant in depth. Mathematically, let $Z_4(k_x,k_y)$ and $Z_6(k_x,k_y)$ be the 4th and 6th Zernike polynomials which correct for defocus and astigmatism at 0° respectively. Then, for each depth z, the volume is refocused according to:

$$S_{AC}(x,y,z) = \mathcal{F}^{-1}\{\tilde{S}_{OCT}(k_x,k_y,z)\exp(i(m_4z+b_4)Z_4 + iz_6Z_6)\},$$

where $S_{AC}$ is the refocused volume, $S_{AC}$ is the original OCT volume, $$m_4 = \frac{(z_4^1 - z_4^2)}{(z^1 - z^2)}; \quad b_4 = z_4^1 - m_4 z^1,$$

and the arguments of the Zernike polynomials are omitted for the sake of conciseness. The foregoing is an example of computational aberration correction, and it is to be understood that the correction of other aberrations using the techniques described in detail above is within the scope of the present invention. It is also understood that computational defocus manifests in a manner similar to aberrations, and therefore any mention of computational aberration correction, unless explicitly stated otherwise, also includes computational defocus correction. That is, defocus can be thought of as a type of aberration.

Example I—Transverse Motion Correction

Figure 3A:
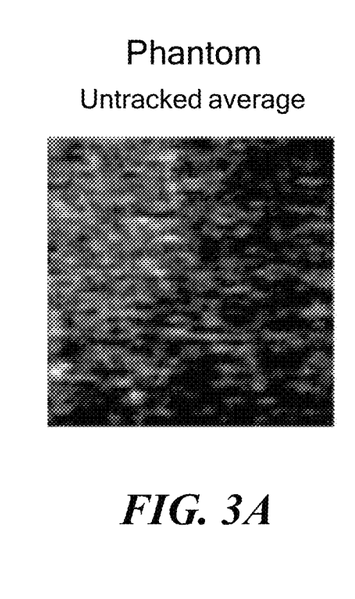
FIGS. 3A and 3C are averages, respectively, of speckle data derived from a tissue phantom and from human finger skin.
Figure 3B:
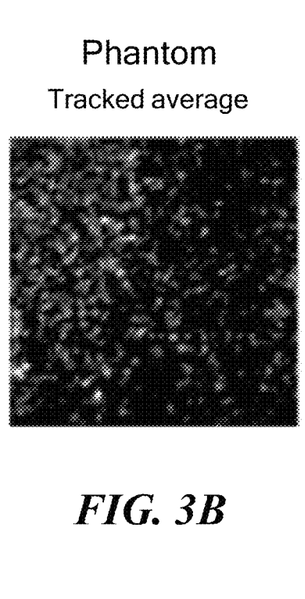
FIGS. 3B and 3D are tracked and motion-corrected versions of FIGS. 3A and 3C.
Figure 3C:
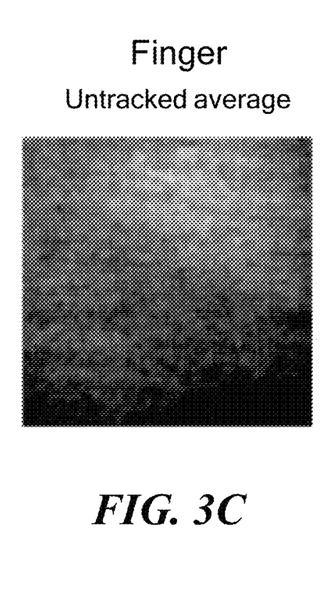

Application of transverse motion based on speckle is shown by acquiring speckle movies 220 (shown in FIG. 2B) both scattering phantoms and in vivo samples, demonstrating that speckle may be accurately tracked. FIGS. 3A and 3C show the averages of 121 frames from two sample videos, the first (FIG. 3A) acquired with a tissue-mimicking phantom made from sub-resolution $TiO_2$ particles in a silicone PDMS gel, and the second (FIG. 3C) was acquired in vivo from skin on a human finger. The concentration of particles in the phantom tissue allowed for sufficient scattering to produce speckle when imaged with the speckle-tracking subsystem. The phantom was placed on a 3-axis translation stage and was moved, in the case shown, along a single axis. After application of the sub-pixel tracking technique described above, the measured displacements were used to stabilize the speckle video and verify proper tracking. The tracked average, shown in FIG. 3B, shows considerably improved contrast relative to the untracked average of FIG. 3A.

Figure 3D:
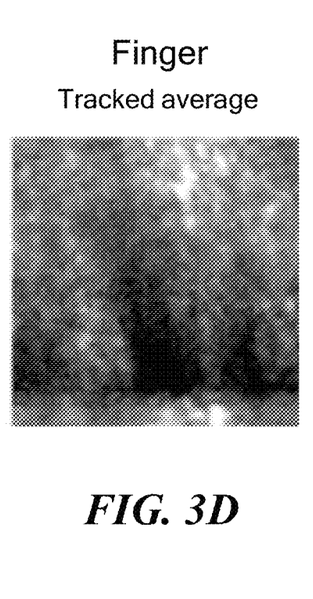

A similar result results in the case of skin on a human finger resting on a kinematic stage and free to move in all dimensions. The unprocessed average for skin on a human finger, shown in FIG. 3C, exhibits a significantly larger degree of motion, and the speckle was observed to be of lower contrast and more dynamic than in the phantom case. Some of the dynamic feature of the speckle is likely due to sub-dermal blood flow which caused the speckle to move and partially wash out during imaging. Even so, there was sufficient stationary speckle to allow for reliable tracking. The tracked average, for the case of human skin, is shown in FIG. 3D.

Calibration between the speckle-tracking subsystem 150 and the OCT system 100 was found to be important. To calibrate the system, a tissue phantom was used. OCT system 100 was set to repeatedly acquire the same frame while the speckle camera acquired images. The phantom was then moved along the fast axis. Two calibration parameters were found to be important. The first was pixel scaling: The number of pixels on the camera which correspond to one pixel in the OCT data. In the experimental system, one pixel of movement on the speckle camera was found to correspond to 1.9 pixels (3.8 μm) in the OCT data. The second parameter was time synchronization: The amount of time delay (measured in OCT frames) from the start of the OCT data to the start of the speckle data. In the experimental system, the speckle tracking data started 2.9 OCT frames (22.7 µs) after the start of the OCT tomogram. The speckle tracking movement was then interpolated to correct for the fractional time delay.

Example II—Transverse Motion Correction

Figure 4A:
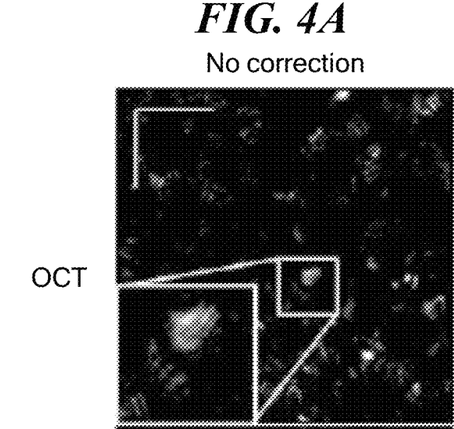
FIGS. 4A, 4B and 4C are, respectively, OCT images of a sample subject to 2-D motion, corrected for the motion in accordance with an embodiment of the present invention, and a control sample not subject to motion.

Reliability of speckle tracking for defocus and aberration correction was demonstrated with the same tissue-mimicking phantom as was used in Example I, now placed on a 3-axis piezoelectric stage and moved in a controlled, sinusoidal manner. While the phantom was only translated in transverse dimensions, small axial vibrations can cause instabilities, and thus the full 3-D correction, described above, was used. With the axial-sectioning capability of OCT, the individual point scatterers can now be resolved, as apparent in the OCT frame shown in FIG. 4A. FIG. 4D shows the effect of computationally refocusing the OCT frame of FIG. 4A, as described above.

Figure 4B:
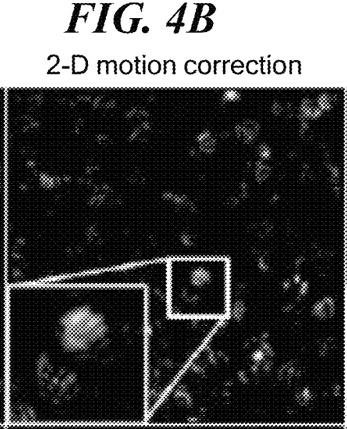
Figure 4C:
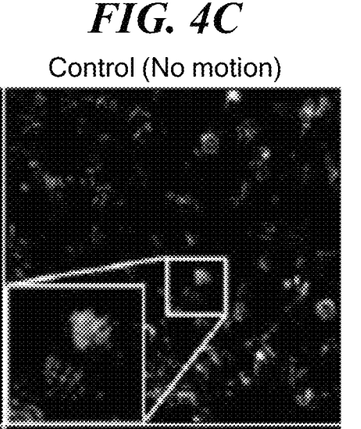
Figure 4D:
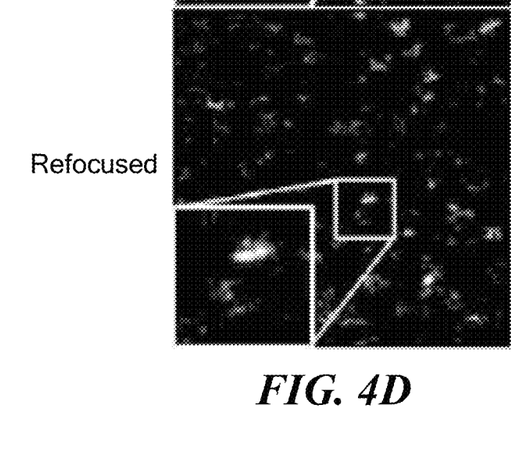
Figure 4E:
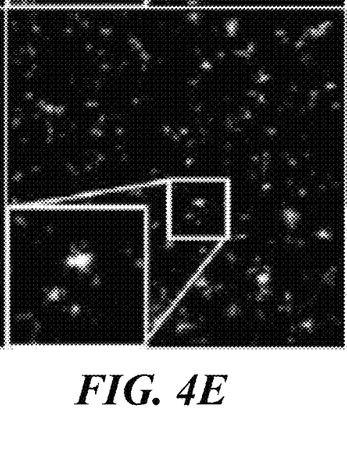
Figure 4F:
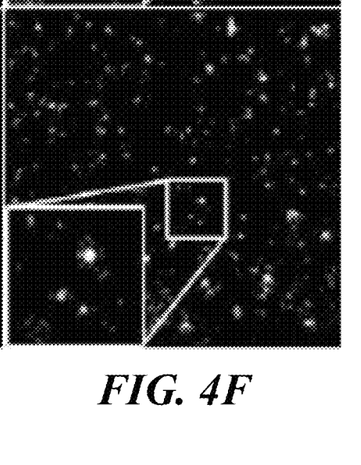

After speckle tracking and two-dimensional motion correction, FIG. 4B shows a less distorted OCT frame, while FIG. 4E shows better refocusing of the corrected frame. For confirmation, a control refocusing experiment where the phantom was not moved while the image in FIG. 4C was obtained, and refocused as shown in FIG. 4F. To show further detail, zoomed insets (2.5×) are included for each image in FIGS. 4A-4E.

Example III—In Vivo 3-D Motion Correction

Figure 5A:
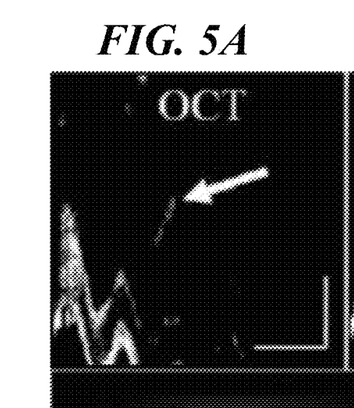
FIG. 5A shows a frame of in vivo OCT data taken on a finger of a human subject.
Figure 5B:
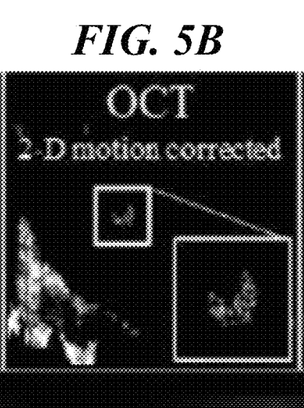
Figure 5C:
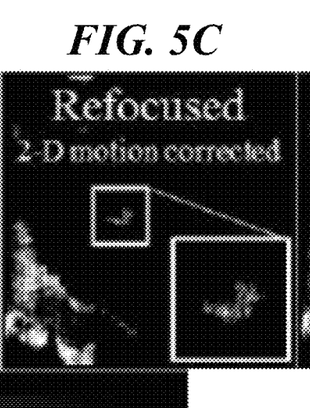

Application of methods of the present invention for correction of motion in all three dimensions has been demonstrated. A volunteer's finger was held in place on top of a kinematic mount, and the mount was translated down so that the volunteer's finger fit between the mount and objective 118 (shown in FIG. 1). This configuration allowed for motion in all three dimensions. The volunteer was asked to gently move his finger dining imaging. Results are now described with reference to FIGS. 5A-5G. FIGS. 5A-5D show a single en face plane. Visible in this en face section is the surface of the tissue (bottom left) and a single sweat duct (center, highlighted with arrow). FIG. 5A shows the original OCT data. FIG. 5B is the same plane as shown in FIG. 5A after using speckle tracking, as described above, for 2-D motion correction. The shape of the sweat duct is recovered.

Figure 5D:
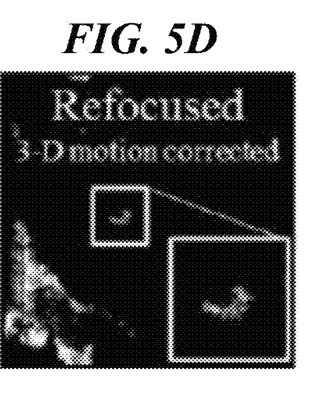
FIG. 5D shows the same plane after motion correction and refocus, in accordance with an embodiment of the present invention.
Figure 5E:
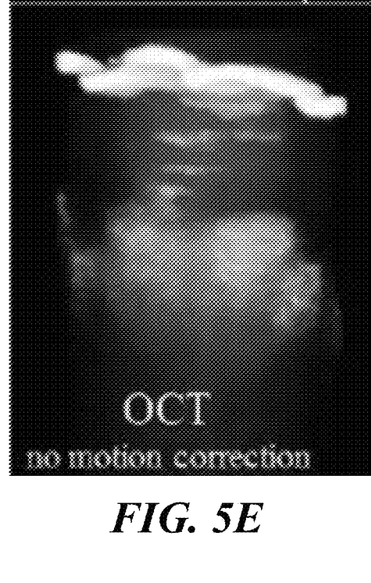
FIGS. 5E and 5F show a single sweat gland in the original OCT data, and as motion corrected and refocused, in accordance with embodiments of the present invention.
Figure 5F:
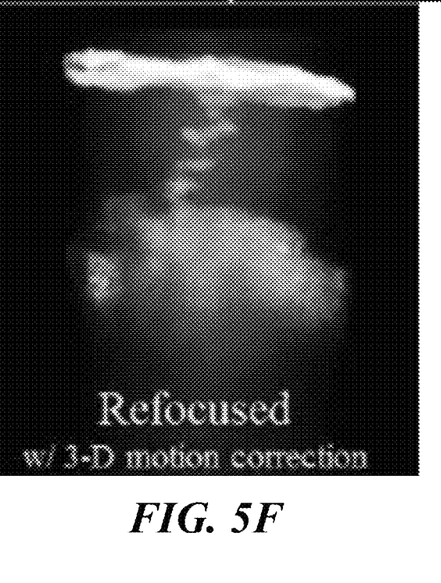
Figure 5G:
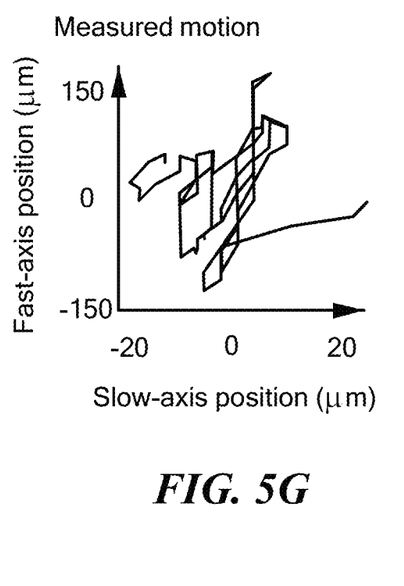
FIG. 5G is a plot of the 2-D tracked motion.

Next, refocusing was performed before phase collection. The plane shown in FIG. 5C exhibits improvement along the fast axis (top-to-bottom), but slight broadening along the slow axis (left-to-right), due to phase errors. Finally, the phase-corrected refocused plane is shown in FIG. 5D. Again, the crescent profile is visible. FIG. 5E shows a 3-D rendering of the original OCT tomogram, and FIG. 5F shows the final refocused tomogram. FIG. 5G is a plot of the 2-D tracked motion.

In various embodiments of the present invention, disclosed methods for analyzing and correcting for motion in coherent imaging systems may be implemented as a computer program product for use with a computer system. Such implementations may include a series of computer instructions fixed either on a tangible medium, such as a computer-readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The embodiments of the invention described above are intended to be merely exemplary; numerous variations and modifications will be apparent to those skilled in the art. All such variations and modifications are intended to be within the scope of the present invention as defined in any appended claims.

We claim:

1. A method for measuring phase variations in a coherent three-dimensional image of a sample, the method comprising:
   a. generating a broadband optical beam incident on the sample along a depth axis;
   b. scanning the broadband optical beam across the sample in a specified scan pattern;
   c. interfering light scattered by the sample with a reference beam derived from the broadband optical beam;
   d. measuring the intensity of the interfered light on at least one photosensitive element;
   e. processing the collected data to generate a cube of complex data including both amplitude and phase data constituting a full tomogram; and
   f. after acquisition of the full tomogram, quantifying generalized motion to the sample based at least on a measured phase variation measured during the course of scanning the broadband optical beam in the specified scan pattern in which phase differences are used to create a 2D phase-variation map and wherein the phase variation is measured based solely on a frame of reference tied to the sample.

2. A method in accordance with claim 1, further comprising correcting the cube of complex data for the generalized motion thereby creating a phase-stable cube of complex data.

3. A method in accordance with claim 2, further comprising at least one of computationally refocusing and computationally correcting aberrations in at least a portion of the phase-stable cube of complex data.

4. A method in accordance with claim 1, wherein the measured phase variation is along an axial direction.

5. A method in accordance with claim 1, wherein scanning the broadband optical beam in the specified scan pattern includes scanning the broadband optical beam across the sample in a transverse plane along a fast axis and a slow axis.

6. A method in accordance with claim 5, further comprising correcting for generalized movement along the fast axis by interpolation of a corresponding frame of the full tomogram.

7. A method in accordance with claim 1, wherein the measured phase variation is derived by:
   a. calculating a plurality of phase differences between A-scans acquired at different points in time;
   b. averaging the complex data along the depth axis and extract the resulting phase to create the 2D phase-variation map; and
   c. integrating a plurality of phase differences along the slow axis to derive a total phase change; and
   wherein for each fixed depth, subtracting the phase variation map from the phase of the complex tomogram.

8. A method in accordance with claim 7, further comprising filtering the 2D phase variation map.

9. A method in accordance with either of claim 1, wherein generating a broadband optical beam incident on the sample includes directing light onto the sample from a source chosen from a group of low-coherence sources including a superluminescent diode, a light-emitting diode, and a broadband laser.

10. A method in accordance either of claim 1, wherein generating a broadband optical beam incident on the sample includes steering the broadband optical beam with a galvanometric steering mirror.

11. A method in accordance with either of claim 1, further comprising correcting at least one of actual and apparent motion in the full tomogram based on the measured phase variation.

12. A method for measuring phase variations in a coherent three-dimensional image of a sample, the method comprising:
   generating a broadband optical beam incident on the sample along a depth axis;
   scanning the broadband optical beam across the sample in a specified scan pattern;
   interfering light scattered by the sample with a reference beam derived from the broadband optical beam;
   measuring the intensity of the interfered light on at least one photosensitive element;
   processing the collected data to generate a plurality of frames of complex data based on the interference of light scattered by the sample with the reference beam at a plurality of axial steps along the depth axis;
   inputting speckle imaging data derived from a surface of the sample at the plurality of axial steps; and
   quantifying phase variations along the depth axis based jointly at least on measured phase fluctuations in an aggregate of the plurality of axial steps and phase statistics of the speckle.

13. A method in accordance with claim 12, further comprising:
   calculating a plurality of phase differences between axial steps along the depth axis;
   averaging the complex data along the depth axis and extracting the phase to create a 2D phase map;
   integrating the plurality of phase differences along a slow axis to derive a total phase change; and
   for each fixed depth, the phase map is subtracted from the phase of the complex tomogram.

14. A method in accordance with claim 13, further comprising correcting for movement along a fast axis by interpolation of a corresponding frame of the full tomogram.

15. A method in accordance with claim 12, further comprising:
   deriving speckle tracking data from intensity of the imaged speckle; and
   correcting the full tomogram for any transverse motion on the basis of the speckle tracking data prior to correction for any motion along the depth axis.

16. A method in accordance with claim 13, further comprising filtering the phase map.

* * * * *

UNITED STATES PATENT AND TRADEMARK OFFICE
CERTIFICATE OF CORRECTION

PATENT NO. : 10,524,663 B2
APPLICATION NO. : 15/185410
DATED : January 7, 2020
INVENTOR(S) : Stephen A. Boppart, Paul Scott Carney and Nathan Shemonski Page 1 of 1

It is certified that error appears in the above-identified patent and that said Letters Patent is hereby corrected as shown below:

In the Claims

In Column 15, Line 18:
Remove "either of"

In Column 15, Line 24:
Replace "in accordance either of"
With "in accordance with"

In Column 15, Line 28:
Remove "either of"

Signed and Sealed this
Fourteenth Day of April, 2020

Andrei Iancu
*Director of the United States Patent and Trademark Office*